United States Patent [19]

Cornell

[11] 4,055,501
[45] Oct. 25, 1977

[54] FLUID COLLECTION DEVICE WITH PHASE PARTITIONING MEANS

[75] Inventor: William D. Cornell, Ballwin, Mo.

[73] Assignee: Sherwood Medical Industries Inc., St. Louis, Mo.

[21] Appl. No.: 649,881

[22] Filed: Jan. 16, 1976

[51] Int. Cl.$^2$ .............................................. B01D 21/26
[52] U.S. Cl. ............................... 210/516; 23/258.5 R; 210/DIG. 23
[58] Field of Search ......... 210/83, 516, 518, DIG. 23, 210/DIG. 24; 23/230 B, 258.5 R, 259 R, 292; 128/214 R, 218 M, 272, DIG. 5

[56] References Cited

U.S. PATENT DOCUMENTS

| | | | |
|---|---|---|---|
| 3,780,935 | 12/1973 | Lukacs et al. ...................... | 210/83 X |
| 3,852,194 | 12/1974 | Zine, Jr. ........................ | 210/DIG. 23 |
| 3,909,419 | 9/1975 | Ayres ........................... | 210/DIG. 23 |
| 3,920,549 | 11/1975 | Gigliello et al. ............. | 210/DIG. 23 |
| 3,957,654 | 5/1976 | Ayres .................................. | 210/516 |

*Primary Examiner*—William A. Cuchlinski, Jr.
*Attorney, Agent, or Firm*—Stanley N. Garber; William R. O'Meara

[57] ABSTRACT

A blood collection device includes a tube for receiving a sample of whole blood for centrifugal separation into the lighter phase, plasma or serum, and the heavier cellular phase. The tube has a needle-pierceable stopper at one end for maintaining a negative pressure in the tube. A blood phase partitioning device is disposed within the tube and includes an upper cylinder member and a lower piston member slidable in the upper member. The cylindrical member has a plurality of peripheral holes therein and a specific gravity greater than that of the piston member, with the members together having a specific gravity between that of the lighter phase and that of the heavier phase. A sealant is disposed within and in direct contact with the cylindrical member and has a specific gravity substantially equal to that of the two members together. During centrifugation of the blood, the partitioning device automatically moves to the interface of the two phases, and the members move relative to each other forcing the sealant radially outwardly through the peripheral holes in the cylindrical member and against the inner wall of the tube to provide a permanent partition between the two separated phases.

16 Claims, 3 Drawing Figures

FLUID COLLECTION DEVICE WITH PHASE PARTITIONING MEANS

BACKGROUND OF THE INVENTION

This invention relates to fluid collection devices and more particularly to blood collection devices having means for partitioning the lighter and heavier phases of blood.

In the testing of blood samples, whole blood is usually drawn into an evacuated tube and the tube placed in a centrifuge for separating the lighter and heavier phases so that the individual phases may be isolated and tested. Many different types of phase partitioning devices which provide a barrier or seal between the separated phases have been used or proposed for the purpose of allowing the lighter phase to be decanted or poured into a transfer tube free of cells, or to enable the two phases to remain in the collection tube without intermixing during shipment to a laboratory where the lighter phase is removed and subjected to analysis.

In U.S. Pat. No. 3,852,194 and U.S. Pat. No. 3,780,935, gel-like materials, such as a silicone material including a silicone fluid and silica powders, is disposed in a collection tube, the gel-like material having a specific gravity between that of the lighter phase and that of the heavier phase so that it flows to the interface of the two phases and forms a partition between them. These devices generally require a relatively large amount of gel-like material, and in addition to the relatively high cost of the material, a relatively large surface area of the material is in contact with the blood components before, during, and after centrifugation. This relatively large surface area of contact tends to increase the danger of interaction between the gel-like material and lighter blood phase which is to be analyzed. For example, collection tubes are used that employ silicone gel-like materials which produce oil in the lighter phase which tends to clog and restrict the flow of fluid in the tubing of blood analyzing equipment, especially in automatic blood analyzers. In U.S. Pat. 3,852,194 there is also disclosed a relatively complicated arrangement which includes a spool member, which may be made of rubber, having a hole through it and which has a wiper for sealing contact with the inner wall of the tube. The spool moves toward the closed end of the tube while the gel-like material moves toward the stopper and closes the hole in the spool member upon separation of the phases.

In U.S. Pat. No. 3,909,419, a plasma separator is used wherein a pair of cylinders are disposed in the container and a plurality of micro encapsulated beads of gelatin are disposed between the cylinders. The specific gravities of the two cylinders and the gelatin beads are such that, by increasing the speed of the centrifuge after the phases have been separated, the cylinders move toward each other and rupture the encapsulated beads to cause the gelatin to form a seal between the cylinders and inner wall of the container at a location between the two phases. This arrangement is relatively expensive since it requires the manufacture of encapsulated beads and also requires centrifugation at two different speeds.

SUMMARY OF THE INVENTION

Accordingly, an object of the present invention is to provide a novel partitioning means for maintaining the lighter and heavier phases of a fluid, such as blood, separated, and which is highly effective, relatively simple, and economical. In accordance with the present invention, a fluid collection device is provided which includes a collection container for receiving a liquid adapted to be centrifugally separated into relatively lighter and heavier phases, a pair of movable members in the container each having a different specific gravity, and a sealant material adapted to be squeezed outwardly from the members. The specific gravity of the two members together is intermediate the specific gravity of the lighter phase and that of the relatively heavy phase, and the specific gravity or the sealant is substantially equal to that of the two members together. The sealant is adapted to be squeezed outwardly from the members and into contact with the interior wall of the container at a location between the separated phases. These as well as other objects and advantages of the present invention will become apparent from the following detailed description and drawing.

DESCRIPTION OF THE PREFERRED EMBODIMENT

Figure 1:
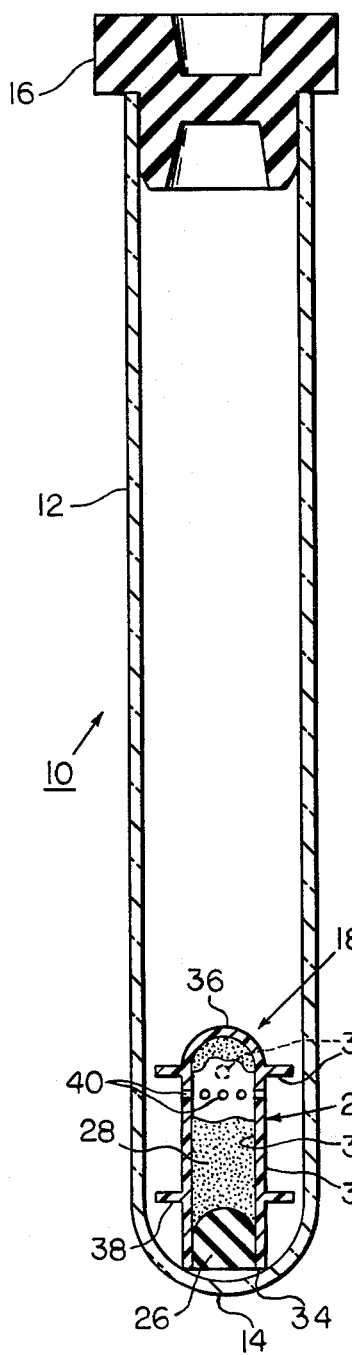
FIG. 1 is an elevational cross-sectional view of a blood collection tube containing a phase partitioning device in accordance with a preferred embodiment of the present invention.

Referring now to the drawing, and especially to FIG. 1, there is shown a fluid collection device 10 including a container or blood collection tube 12 which is preferably of transparent glass and which is shown closed at the bottom by an integral portion 14 of the tube. The tube 12 has an upper open end that is closed by a closure or stopper 16 which extends into the open end in sealing engagement with the side walls of the tube. The stopper 16 is pierceable by a needle and self-sealing, and may be formed of a suitable elastomer, such as butyl rubber. The collection tube is provided with a desired negative pressure or partial vacuum that is maintained by the stopper 16. Disposed within the tube 12 is a movable blood phase partitioning or separation device 18.

Figure 2:
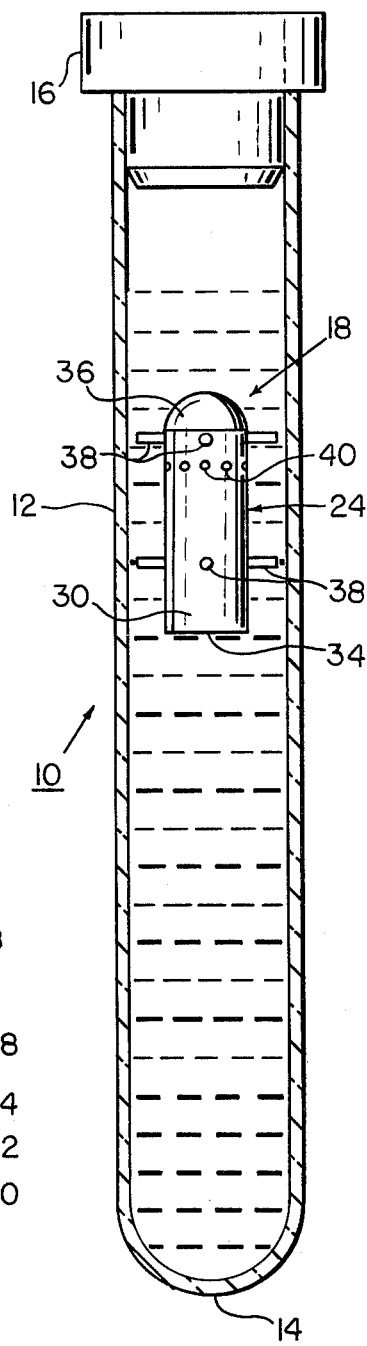
FIG. 2 is an elevational cross-sectional view of the collection tube of FIG. 1 after blood has been drawn into it and during an intermediate stage in the centrifugation of the blood.
Figure 3:
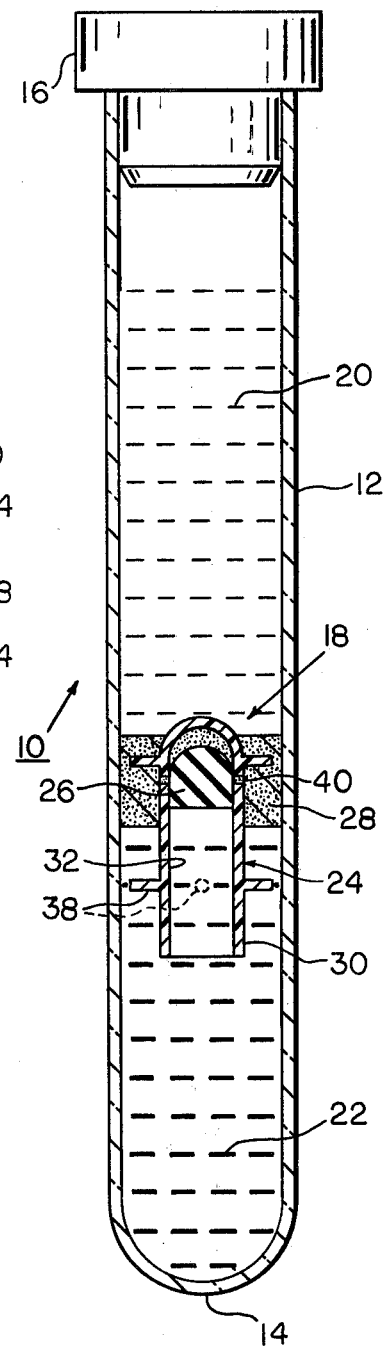
FIG. 3 is an elevational cross-sectional view of the collection tube shown in FIG. 3 but after complete phase separation of the blood.

A sample of blood may be drawn into the blood collection device 10 by use of a double-ended needle cannula or a conventional needle holder and tube guide device (not shown) having a double-ended needle cannula. For example, after the distal pointed end of the needle cannula is inserted into the vein of a patient, the device 10 is moved within the holder until the proximal pointed end of the needle cannula has pierced the stopper 16 and communicates with the interior of the tube 12, whereupon blood flows into the tube. The filled tube is removed from the holder and placed in a centrifuge such that the lower end 14 will be radially outwardly of the stopper and axis of rotation of the centrifuge during certifugation. The phase partitioning device 18 will automatically move within tube 12 during centrifugation, for example, as illustrated in FIGS. 2 and 3, with the device 18 forming a partition or barrier across the tube in its final position (FIG. 3) upon complete separation of the blood into its lighter phase 20, serum or plasma, and its heavier cellular phase 22, as will be more fully discussed hereinafter.

The phase partitioning device 13 includes an upper, generally cylindrical member 24, a lower piston member 26, and a gel-like sealant material 28. The upper hollow member includes a cylindrical body portion 30 having interior walls defining a chamber or bore 32 having an open lower end 34 closed by the piston member 26 in FIG. 1, and an upper end closed by an integral, domed portion 36 having its highest point on the vertical axis of the device 18. The domed portion prevents cells from being trapped on the upper end of the device. The sealant 28 is disposed in bore 32 between the member 26 and the domed portion 36. The member 24 has a plurality of integral stabilizing extensions shown as integral radially outwardly extending stabilizing pins indicated at 38. Four pins 38 are shown adjacent the upper end of member 24 circumferentially spaced 90° apart, and another set of four pins 38 are shown similarly spaced apart adjacent the lower end of the member 24. The pins 38 maintain the device 18 in a desired orientation, such as substantially centered along the vertical axis of the tube. The body portion 30 is also provided with a plurality of equally circumferentially spaced openings or holes 40 extending around the upper portion of the cylindrical body portion 30. These holes extend radially through the side walls of the member 24 and are arranged so that the sealant 28 flows radially through these holes to provide an even distribution of the sealant around the member 24, as will be described hereinafter.

The two members 24 and 26 are formed so that the average specific gravity of the two members together is intermediate the specific gravity of the separated lighter phase of blood 20, and that of the separated heavier cellular phase 22. Also, the sealant 28 is formed of a material, as will be further discussed, that has a specific gravity which is intermediate the specific gravities of the two phases and substantially equal to the average specific gravity of the two members together. Because the specific gravity of the device 18, that is, of the two members 24 and 26, and sealant 28 together, is intermediate that of separated light and heavy phases, the device 18 will move during centrifugation and arrive at the interface of the two phases upon complete separation of the phases. The specific gravity of the device 18 may be made slightly less than that of whole blood so that the device will tend to start at the top or radially inner end of the blood column. The upper member 24 is made to have a specific gravity greater than that of the lower member 26. The device 18, when placed in the tube 12, is oriented with the member 26, which has a lower specific gravity than that of member 24, disposed at the bottom of the tube, as viewed in the drawing, and which is on the radially outer side of the sealant 28 during centrifugation. With this construction and orientation, the density of the fluid below or radially outwardly of the device 18 increases centifugation, and the two members 24 and 26 move relative to each other because they have different specific gravities, the member 26 moving within bore 32 toward the domed portion 36 of the member 24. This relative movement of the members 24 and 26 causes the interior surface of the dome portion 36 and the spaced facing upper or interior surface of the member 26 to move toward each other and reduce the space between them to thereby cause the sealant 28 to be extruded or squeezed outwardly through holes 40 and into contact with the interior side walls of the tube 12 at the interface of the separated phases 20 and 22, as indicated in FIG. 3. The members 24 and 26, and the sealant 28, together, form a permanent partition or barrier sealing the separated phases from each other. Since the sealant 24 has a specific gravity between that of the lighter phase and that of the heavier phase, it seeks its own specific gravity level between the two phases and forms a seal entirely around the member 24 between the member and the tube.

While various types of sealant materials may be used, the sealant 28 should be substantially hydrophobic, inert with respect to the blood phases, and, of course, flowable under pressure conditions such as when the members 26 moves upwardly in member 24 as indicated in the drawing. The viscosity or consistency of the sealant 28, the size of holes 40, and the difference between the specific gravities of members 24 and 26, are chosen such that complete phase separation has taken place or all cells have passed the device 18, before the sealant 28 is extruded out into sealing contact with the inner wall of the tube 12. Sealant 28, however, should be substantially non-flowable at rest or after centrifugation and subsequent handling, such as tipping of the tube, or during mailing of the tube. Sealant or gel-like materials may be of the types disclosed in the previously mentioned U.S. patents. For example, gel-like materials of the type disclosed in U.S. Pat. No. 3,852,194 and which include a mixture of silicone fluid and a powdered inorganic filler such as hydrophobic silica powder may be used.

Another material which may be used as a sealant is disclosed in copending application U.S. Ser. No. 642,514, filed Dec. 19, 1975, and also in copending application U.S. Ser. No. 649,880, filed on the same day as this application and entitled "Blood Phase Separation Means," and assigned to the assignee of this application. This material includes a hydrocarbon polymer such as liquid polybutene, a hydrophobic silica powder, and a hydrophillic silica powder in proportions to provide a sealant having a desired consistency and a specific gravity between the specific gravities of the lighter and heavier blood phases. Other materials, for example, other hydrocarbon polymers, such as liquid butyl rubber and liquid polybutadiene, mixed with suitable fillers, such as hydrophillic and hydrophobic silica, as described in the above application, generally may also be used as a sealant in device 18.

One specific example of a useful sealant which is described in the above copending application, includes 100 parts by weight of liquid polybutene (Polybutene Grade 24 - Chevon Chemical Co. of San Francisco, Calif., 20 parts by weight of hydrophillic silica powder (Min-U-Sil-10, PGS, a subsidiary of ITT, Pittsburgh, Pa.), and 9 parts by weight of a hydrophobic silica powder (Aerosil R-972, Degussa Inc., Pigments Division, New York, N.Y. This sealant generally did not produce oil in the light phase or only rarely.

Since the specific gravity of whole blood is generally about 1.05, that of the light phase about 1.03, and that of the heavier phase about 1.08, the average or total specifiic gravity of the device 18 may be about 1.05 or slightly less as previously mentioned herein. The specific gravity of the two members 24 and 26 together may be about 1.05. The specific gravity of the sealant material 28 may also be about 1.05. The materials used in forming the members 24 and 26 should also be inert with respect to the separated blood phases. Various types of materials are useful in forming these members and each may be formed or molded of one of more plastic materials. The cylindrical member 24 may be formed of a relatively rigid plastic such as poly methylmethacrylate or styrene acrylonitrile. The piston member 26 may be formed of a suitable elastomer or rubber material.

In one case, the liquid polybutene based sealant described in the above specific example was used in a cylindrical member of the above styrene acrylonitrile that had a specific gravity of 1.08. The cylindrical member had about 16 holes (40), each having a diameter of about 0.025 inch. The piston member was formed of an elastomer having a specific gravity of about 0.94. This partitioning device provided a good seal between the phases.

The partitioning device 18 may be advantageously inserted during manufacture of the blood collection device so that the stopper 16 does not have to be removed to insert the device into the tube 12. Where the dimensions of device 18 permit a blood clot to pass it during centrifugation, the blood collection device can be used for both plasma and serum. Where the size of the partitioning device relative to the tube does not permit a blood clot to pass by it, the device 18 may be inserted in tube 12 after the blood has been inserted into the tube and a clot formed or a tube having a removable stopper at each end may be used. In the latter case, blood can, for example, be inserted through one stopper and the collection device centrifuged such that the heavier phase moves toward that stopper, and then the lighter phase can be removed by removing the stopper at the opposite end of the tube.

Where the total specific gravity of device 18 is less than the average specific gravity of whole blood (but intermediate the specific gravities of the separated phases), it will rise to the top of the whole blood when the tube is in its upstanding position as shown, and the clot or major portion thereof will generally form below it. In such case, the clot or major portion of the clot will generally not have to pass the partitioning device if the tube is vertically positioned after receiving whole blood, and especially where a blood clot activating material is disposed in the bottom of the tube.

The piston member 26 may be sized to sealingly slide within and engage the walls of the cylindrical member 24 as in indicated in the drawing. With the piston member closing the bottom of the member 24 and the domed portion 36 closing or substantially closing the top, the sealant material is substantially entirely enclosed, except for the row of small holes 40, when the device in in its initial condition (FIG. 1). Thus, only a relatively small surface area of the sealant in the illustrated device is exposed to external fluids. Even during and after centrifugation, the surface area of the sealant in contact with the phases is relatively small since the members 24 and 26 form portions of the partitioning device. Since the surface area of contact between the sealant and liquids in the tube is relatively small, there is less chance of undesirable interaction, if any, between the sealant material used and either phase of blood.

The size, number, arrangement, shape, and location of the holes 40 may be varied from that shown in the drawing. For example, some holes may be slotted for formed in the domed portion 36. Also, depending upon the design and shapes of the upper and lower members of device 13, the sealant 28, which is generally tacky, such as in the case of the materials described herein, may be in direct contact with both of the members 24 and 26 before centrifugation so that the sealant holds the members together. The sealant 28 is a generally homogeneous mixture of materials, which mixture is the only material used with the members 24 and 26. In the case of the encapsulated beads disclosed in U.S. Pat. No 3,909,419, the shell or covering material of each bead is in direct contact with the upper and lower members, but the sealant or gelatin within the shell material is not in contact with either member before centrifugation.

As various changes could be made in the above construction without departing from the scope of the invention, it is intended that all matter contained in the above description or shown in the accompanying drawing shall be interpreted as illustrative and not in a limiting sense.

What is claimed is:

1. A blood collection device for receiving a sample of blood adapted to be centrifugally separated into a lighter phase and a heavier cellular phase comprising a closed container tube for receiving the sample of blood, means closing one end of said tube, a needle-pierceable stopper closing the other end of said tube, and a phase partitioning device within said closed tube including first and second relatively movable members having axially spaced facing surfaces and a combined average specific gravity intermediate that of the lighter phase and that of the heavier phase and with said first member having a specific gravity greater than that of said second member, and a flowable sealant disposed between said facing surfaces in direct contact with one of said members before centrifugation, said sealant having a specific gravity substantially equal to said combined average specific gravity, both of said members having a width substantially less than the inner diameter of said tube to allow fluid to readily flow by said partitioning device during separation of the phases, one of said members having a plurality of circumferentially spaced, radially outwardly extending stabilizing means thereon for maintaining said partitioning device in a substantially predetermined orientation in said tube during centrifugation of the collection device, said partitioning means being movable to a position in said tube adjacent the interface of the phases and said sealant being squeezeable generally radially outwardly from between said facing surfaces and into contact with the inner wall of said tube in response to the relative movement of said spaced surfaces of said members toward each other due to centrifugal forces during centrifugation of the collection device to provide, with said first and second members, a partition sealing the heavier phase from the lighter phase.

2. The blood collection device of claim 1 wherein said one member is hollow, and the other of said members is movable in said hollow member.

3. The blood collection device of claim 2 wherein said spaced facing surfaces are within said hollow member, and said hollow member has openings through the side wall thereof for the flow of said sealant therethrough.

4. The device of claim 3 wherein said hollow member is said first member.

5. The blood collection device of claim 1 wherein said first member includes a clindrical portion having one end open and the opposite end substantially closed, said second member being a piston slidable in said cylindrical portion, said cylindrical portion having a plurality of circumferentially arranged openings in the side wall thereof adjacent to said closed end of said cylindrical portion.

6. The blood collection device of claim 5 wherein said stabilizing means includes first and second sets of radially outwardly extending circumferentially spaced pin members with said sets being axially spaced from each other.

7. The blood collection device of claim 1 wherein said sealant is flowable in response to the movement of said spaced facing surfaces toward each other during centrifugation and is substantially non-flowable after centrifugation.

8. The blood collection device of claim 1 wherein said tube has a negative pressure therein, and said needle-pierceable stopper maintains the negative pressure in said tube.

9. The blood collection device of claim 1 wherein the total specific gravity of said phase partitioning device is less than the average specific gravity of whole blood so that said phase partitioning device will rise to the top of whole blood when said tube is in an upstanding position.

10. The blood collection device of claim 1 wherein said sealant is a generally homogeneous mixture of materials, and said mixture is the only material besides said first and second members used in said partitioning device.

11. The blood collection device of claim 10 wherein said mixture is tacky and in direct contact with both of said first and second members.

12. The blood collection device of claim 1 wherein said means closing one end of said tube is an integral portion of said tube.

13. The blood collection device of claim 12 wherein said tube has a negative pressure therein for drawing whole blood into said tube when said stopper is pierced by a cannula connected with a source of whole blood, and wherein one end of said first member faces said stopper and is between said second member and said stopper.

14. The blood collection device of claim 13 wherein first member has a cylindrical body portion containing said sealant and is closed at said one end thereof and has circumferentially spaced openings through the side walls thereof for the flow of said sealant therethrough, and said second member is a piston slidable in said body portion.

15. The blood collection device of claim 1 wherein one end of said first member faces said stopper and is generally domed-shaped so that cells will tend to slide off said first member.

16. A blood collection device for receiving a sample of blood adapted to be centrifugally separated into a lighter phase and a heavier cellular phase comprising a container tube for receiving the sample of blood and having one end integrally closed, a needle-pierceable stopper sealingly closing the opposite end of said tube, said tube having a negative pressure therein for drawing whole blood into said tube when said stopper is pierced by a cannula connected to a source of whole blood, and a phase partitioning device within said tube including first and second relatively movable members having axially spaced facing surfaces respectively, and a flowable sealant having a specific gravity intermediate those of the lighter and heavier phases disposed between said facing surfaces in direct contact with one of said members before centrifugation of the collection device, said partitioning device having a specific gravity which is less than that of whole blood so that it tends to float to the top of the whole blood when whole blood is received in said tube and which is intermediate the specific gravities of the two phases so that during centrifugation said partitioning device moves to a location adjacent to the interface of the two phases, both of said first and second members having a width substantially less than the inner diameter of said tube so that the lighter phase can readily flow past said partitioning device during centrifugation, said first member having stabilizing members extending radially outwardly from the radial outer walls thereof which are circumferentially spaced from each other to maintain said partitioning device substantially centered along the longitudinal axis of said tube, said first member having a specific gravity greater than that of said second member so that said sealant is squeezeable generally radially outwardly from between said facing surfaces and into contact with the inner wall of said tube in response to the relative movement of said spaced surfaces of said members toward each other due to centrifugal forces during centrifugation of the collection device to provide, with said first and second members, a partition sealing the heavier phase from the lighter phase.

* * * * *